(12) United States Patent
Ono et al.

(10) Patent No.: US 6,348,600 B1
(45) Date of Patent: Feb. 19, 2002

(54) METHODS FOR MAKING OPTICALLY ACTIVE 3-AMINOPYRROLIDINE-2,5-DIONE DERIVATIVE AND OPTICALLY ACTIVE 3-AMINOPYRROLIDINE DERIVATIVE

(75) Inventors: Takae Ono; Haruyo Sato, both of Aichi (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/788,944

(22) Filed: Feb. 20, 2001

(51) Int. Cl.⁷ .............................................. C07D 207/50
(52) U.S. Cl. ........................................ 548/545; 548/546
(58) Field of Search ................................. 548/545, 546

(56) References Cited

U.S. PATENT DOCUMENTS

| | | | | |
|---|---|---|---|---|
| 5,585,500 A | * | 12/1996 | Drauz et al. .................. | 548/541 |
| 5,670,656 A | * | 9/1997 | Cox et al. ..................... | 548/543 |
| 5,912,358 A | * | 6/1999 | Frohn et al. .................. | 548/543 |
| 5,977,381 A | * | 11/1999 | Klinkhammer et al. ...... | 548/557 |

FOREIGN PATENT DOCUMENTS

EP  0 302 372 A  2/1989

OTHER PUBLICATIONS

Kavalek, J. et al., Kinetics and mechanism of Reversible, Base–Catalyzed Ring Closure of 3–(Methoxycarbonyl)propionanilide and 0–(methoxycarbonylmethyl)–N–phenyl-carbamate. COLLECT. CZECH. CHEM. COMMUN., vol. 54, no. 4, 1989, pp. 1005–1011.

\* cited by examiner

*Primary Examiner*—Floyd D. Higel
*Assistant Examiner*—Golam M. M. Shameem
(74) *Attorney, Agent, or Firm*—Schnader Harrison Segal & Lewis LLP

(57) ABSTRACT

A method for making an optically active 3-aminopyrrolidine-2,5-dione derivative represented by the formula (3) includes cyclizing an optically active asparagine ester derivative represented by the formula (1) or (2), or an acid salt thereof. A method for making an optically active 3-aminopyrrolidine derivative represented by the formula (9) includes reducing the optically active 3-aminopyrrolidine-2,5-dione derivative represented by the formula (3). A method for making an optically active 3-aminopyrrolidine derivative includes hydrogenolyzing the optically active 3-aminopyrrolidine derivative represented by the formula (9).

22 Claims, No Drawings

METHODS FOR MAKING OPTICALLY ACTIVE 3-AMINOPYRROLIDINE-2,5-DIONE DERIVATIVE AND OPTICALLY ACTIVE 3-AMINOPYRROLIDINE DERIVATIVE

BACKGROUND OF THE INVENTION

1. Field of the Invention

The present invention relates to a method for making optically active 3-aminopyrrolidine derivatives which are useful as raw materials for drugs and agrochemicals and to a method for making optically active 3-aminopyrrolidine-2,5-dione derivatives which are important intermediates thereof.

2. Description of the Related Art

Examples of the known methods for making optically active 3-aminopyrrolidine derivatives include a method in which racemic 1-benzyl-3-aminopyrrolidine is optically resolved by an optical active carboxylic acid. However, since the racemic 1-benzyl-3-aminopyrrolidine, which has been produced by a complex route, is further optically resolved, the method is expensive. Therefore, a method for making optically active 3-aminopyrrolidine derivatives inexpensively has been desired.

Examples of the known methods for making optically active 3-aminopyrrolidine-2,5-dione derivatives includes a method in which N-benzyloxycarbonyl-L-asparagine methyl ester is reacted with 0.95 equivalent of sodium hydroxide to produce (S)-3-benzyloxycarbonylaminopyrrolidine-2,5-dione, and then by way of the reaction described below, (S)-3-benzyloxycarbonylaminopyrrolidine is produced as disclosed in Tetrahedron; Asymmetry Vol. 3, 1239–1242 (1992). A method for producing a compound having a substituent in the first position is also disclosed in the same document, in which N-benzylation is carried out by the subsequent interphase reaction in the presence of a quaternary ammonium salt as shown below.

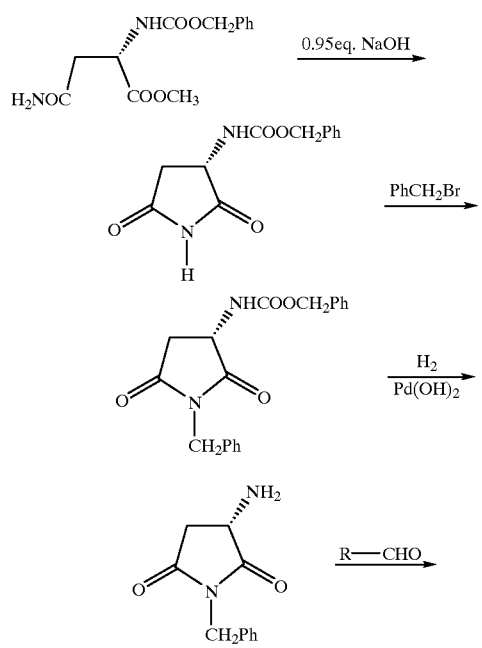

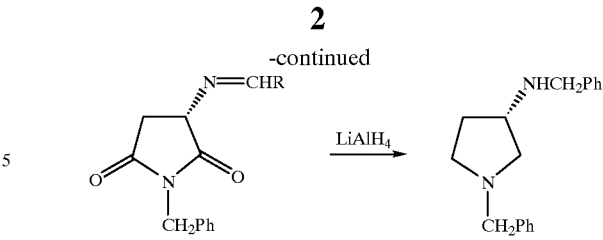

Although the above method, which has high reaction selectivity, is superior in making optically active 3-aminopyrrolidine derivatives, it is difficult to employ the method for industrial use because (1) expensive L-asparagine is used as a starting material; (2) the number of process steps is increased, which is troublesome; and (3) a moisture-sensitive, expensive reducing agent (LiAlH$_4$) is used.

SUMMARY OF THE INVENTION

It is an object of the present invention to provide methods for making optically active 3-aminopyrrolidine-2,5-dione derivatives and optically active 3-aminopyrrolidine derivatives from inexpensive raw materials, with a decreased number of process steps, in high yields, and with high optical purity.

The present inventors have carried out thorough research to overcome the difficulties described above and have achieved the present invention.

In one aspect of the present invention, a method for making an optically active 3-aminopyrrolidine-2,5-dione derivative represented by the following formula (3) includes cyclizing an optically active asparagine ester derivative represented by the following formula (1), an optically active isoasparagine ester derivative represented by the following formula (2) which is an isomer thereof, a mixture of these substances, or an acid salt of these substances:

wherein $R^1$ is a lower alkyl group having 1 to 4 carbon atoms, an aryl group, or an aralkyl group; each of $R^2$ and $R^3$ is a hydrogen atom, an alkyl group, an aryl group, an aralkyl group, an acyl group, an alkoxylcarbonyl group, an alkylsulfonyl group, an arylsulfonyl group, or an aralkylsulfonyl group, $R^2$ and $R^3$ being the same or different; $R^4$ is an alkyl group having 1 to 3 carbon atoms; and the carbon atom with the asterisk * is an asymmetric center.

In another aspect of the present invention, a method for making an optically active 3-aminopyrrolidine derivative represented by the following formula (9) includes reducing an optically active 3-aminopyrrolidine-2,5-dione derivative represented by the formula (3):

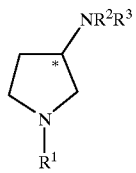 (9)

wherein $R^1$, $R^2$, $R^3$, and the asterisk * are the same as those in the formula (1).

In another aspect of the present invention, a method for making an optically active 3-aminopyrrolidine derivative, in which the first position is unsubstituted, includes hydrogenolyzing an optically active 3-aminopyrrolidine derivative represented by the formula (9), wherein $R^1$ is a substituted or unsubstituted benzyl group.

DESCRIPTION OF THE PREFERRED EMBODIMENTS

In the present invention, either the optically active asparagine ester derivative represented by the formula (1) or the optically active isoasparagine ester derivative represented by the formula (2) is referred to as an optically active asparagine ester derivative. Additionally, either an optically active asparagine derivative represented by the formula (6) below or an optically active asparagine derivative represented by the formula (7) below which is an isomer thereof is referred to as an optically active asparagine derivative.

These compounds also include optically active substances in which either the L-form (S-form) or the D-form (R-form) is in excess and also include an acid salt thereof.

The optically active 1-substituted-3-aminopyrrolidine-2,5-dione derivative represented by the formula (3), the optically active 1-substituted-3-aminopyrrolidine derivative represented by the formula (9), and the optically active 3-aminopyrrolidine derivative in which the first position is unsubstituted also include optically active substances in which either the L-form (S-form) or the D-form (R-form) is in excess and also include an acid salt thereof. The optical purity of the optically active substances is !preferably 80% e.e. or more, and more preferably 90% e.e. or more.

In the present invention, the optically active asparagine ester derivative represented by the formula (1) or (2), or an acid salt thereof is cyclized to produce the optically active 3-aminopyrrolidine-2,5-dione derivative represented by the formula (3). In such a method, it is not necessary to protect or deprotect an amino group in the third position, and also it is possible to produce an optically active 3-aminopyrrolidine-2,5-dione derivative from the optically active asparagine ester derivative represented by the formula (1) or (2) with a decreased number of process steps, in high yields, and with high optical purity.

In the formula (1), $R^1$ is preferably a lower alkyl group having 1 to 4 carbon atoms, a substituted or unsubstituted phenyl group, or a substituted or unsubstituted benzyl group, and is more preferably a substituted or unsubstituted benzyl group. Each of $R^2$ and $R^3$ is a hydrogen atom, an alkyl group, an aryl group, an aralkyl group, an acyl group, an alkoxylcarbonyl group, an alkylsulfonyl group, an arylsulfonyl group, or an aralkylsulfonyl group, and $R^2$ and $R^3$ may be the same or different as described above. When $R^2$ is any one of an acyl group, an alkoxylcarbonyl group, an alkylsulfonyl group, an arylsulfonyl group, and an aralkylsulfonyl group, $R^3$ is preferably a hydrogen atom. Preferably, as the aryl group, a substituted or unsubstituted phenyl group is selected, and as the aralkyl group, a substituted or unsubstituted benzyl group is selected.

Each of the compounds represented by the formula (1) and (2) may be used alone or the compounds may be used as a mixture thereof in any mixing ratio. Preferably, the compounds have an optical purity of 90% e.e. or more.

The cyclization may be carried out in an organic solvent or in water. Preferably, the cyclization is carried out in an aqueous solution in which an organic solvent and water are mixed. The pH of the reaction liquid is preferably 3 to 8, more preferably 5 to 7.5, and most preferably 6 to 7. The pH may be adjusted after an acid salt of the optically active asparagine ester derivative is dissolved into an aqueous solution. Alternatively, after the optically active asparagine ester derivative is dissolved in the aqueous solution in which the pH is preliminarily adjusted, the pH may be finely adjusted again. As the organic solvent, although any compound which is inert in the reaction and which is dissolved in water homogeneously may be used, preferably, a lower alcohol, such as methanol or ethanol, or a water-soluble ether, such as tetrahydrofuran or glyme, is used, and more preferably, methanol is used.

Preferably, the pH of the reaction liquid is adjusted by adding an alkali metal salt to the reaction liquid because the yield and the optical purity of the optically active 3-aminopyrrolidine-2,5-dione derivative produced are further increased. As the alkali metal salt, an alkali metal organic acid salt, such as sodium formate, potassium formate, sodium acetate, or potassium acetate; an alkali metal carbonate, such as sodium carbonate or potassium carbonate; an alkali metal hydrogencarbonate, such as sodium hydrogencarbonate or potassium hydrogencarbonate; or a mixture thereof may be used. Preferably, sodium acetate, sodium carbonate, or sodium hydrogencarbonate is used, and more preferably, sodium hydrogencarbonate is used.

The reaction temperature is preferably in the range of 0 to 80° C., and more preferably 20 to 60° C. The reaction time, which depends on the type of starting material and on the reaction conditions, is 0.1 to 30 hours. Although the racemization rate in the cyclizing reaction slightly differs depending on the pH of the reaction mixture, the reaction time, the type of alkali metal salt to be added, etc., by using the production method described above, it is possible to produce the optically active 1-substituted-3-aminopyrrolidine-2,5-dione derivative represented by the formula (3) having an optical purity of 80% e.e. or more. If the optically active asparagine ester derivative used represented by the formula (1) or (2) has an optical purity of 95% e.e. or more, it is possible to obtain the optically active 1-substituted-3-aminopyrrolidine-2,5-dione derivative represented by the formula (3) having an optical purity of 90% e.e. or more.

In order to isolate the optically active 1-substituted-3-aminopyrrolidine-2,5-dione derivative from the reaction mixture, any known method may be used. For example, the reaction mixture is adjusted to be weakly basic, and then extraction is performed using an organic solvent. As the organic solvent, although any compound which is stable during the extraction may be used, for example, toluene or chloroform is preferably used. When the amino group in the third position is basic in the compound represented by the formula (3), it is possible to isolate as an acid salt thereof. When the substituent in the first position in the optically active 1-substituted-3-aminopyrrolidine-2,5-dione derivative represented by the formula (3) is an aryl group or an aralkyl group, e.g., optically active 3-amino-1-benzylpyrrolidine-2,5-dione, since extraction is easily performed using the organic solvent, isolation and purification are facilitated. The concentrate obtained by subjecting the extract to vacuum concentration may be used as it is in the subsequent step.

By reducing the optically active 1-substituted-3-aminopyrrolidine-2,5-dione derivative represented by the formula (3) thus produced, it is possible to produce the optically active 1-substituted-3-aminopyrrolidine derivative represented by the formula (9).

As the optically active 1-substituted-3-aminopyrrolidine-2,5-dione derivative used represented by the formula (3), the one which is isolated and purified, the concentrate of the extract, or an acid salt thereof may be used. The compound preferably has an optical purity of 81% e.e. or more.

As the reaction solvent used an ether, such as tetrahydrofuran, glyme, diglyme, or butanol, may be used. Preferably, tetrahydrofuran, glyme, or diglyme is used, and more preferably, glyme is used.

As the reducing agent, aluminum lithium hydride or a boron hydride may be used. Preferably, the boron hydride which is chemically stable and easy to handle is used. Preferred examples of the boron hydrides include diborane, borane diethyl ether, borane dimethyl sulfide, and sodium borohydride. When sodium borohydride is used, an activating reagent, such as sulfuric acid or trifluoroboron, may be added thereto. The reaction temperature is preferably in the range of −20 to 80° C., and more preferably in the range of −10 to 30° C. The reaction time, which depends on the conditions, is usually 3 to 20 hours.

After the reaction is complete, the produced optically active 1-substituted-3-aminopyrrolidine derivative may be isolated by a known method. For example, after methanol is added to the reaction mixture, concentration is performed to decompose and remove excess borane. The concentrate is dissolved in water and is adjusted to be basic, and extraction is performed using chloroform, and thus the optically active 1-substituted-3-aminopyrrolidine derivative is extracted in a chloroform layer. By concentrating the resultant chloroform layer, the optically active 3-aminopyrrolidine derivative is obtained. By using the production method described above, the optically active 1-substituted-3-aminopyrrolidine derivative represented by the formula (9) having an optical purity of 80% e.e. or more can be obtained. If the optically active 1-substituted- 3-aminopyrrolidine-2,5-dione derivative represented by the formula (3) used has an optical purity of 92% e.e. or more, it is possible to obtain the optically active 1-substituted-3-aminopyrrolidine derivative represented by the formula (9) having an optical purity of 90% e.e.

In the optically active 1-substituted-3-aminopyrrolidine derivative represented by the formula (9) thus obtained, when the substituent in the first position is a substituted or unsubstituted benzyl group, by performing hydrogenolysis in the presence of a noble metal catalyst, an optically active 3-aminopyrrolidine derivative in which the first position is unsubstituted is produced.

As the noble metal catalyst, palladium supported by activated carbon is preferably used. The hydrogen pressure is preferably 0.1 to 5 MPa and more preferably 0.5 to 1 MPa.

The hydrogenolysis is preferably performed In a solvent. As the solvent, an alcohol such as methanol or ethanol, an ether such as tetrahydrofuran, or an aromatic hydrocarbon such as toluene is preferably used. More preferably, methanol or ethanol is used.

The reaction temperature is preferably in the range of 20 to 100° C., and more preferably in the range of 40 to 70° C. The reaction time, which depends on the conditions, is usually 3 to 20 hours.

After the reaction is complete, the produced optically active 3-aminopyrrolidine derivative may be isolated by a known method. For example, after the reaction mixture is filtered to remove the noble metal catalyst, concentration and distillation are performed, and thus the optically active 3-aminopyrrolidine derivative is obtained. By using the production method described above, the optically active 3-aminopyrrolidine derivative having an optical purity of 80% e.e. or more can be obtained.

In accordance with the methods described above, it is possible to produce optically active 3-aminopyrrolidine derivatives and optically active 3-aminopyrrolidine-2,5-dione derivatives which are the intermediates thereof from the optically active asparagine ester derivative represented by the formula (1) or (2) with a decreased number of process steps, in high yields, and with high optical purity. In the reduction reaction, a boron hydride which is chemically stable and easy to handle can be used as the reducing agent, which is also advantageous.

In the present invention, the optically active asparagine ester derivative represented by the formula (1) or (2) can be produced using inexpensive optically active aspartic acid as a starting material, which is also advantageous. In the present invention, although the optically active aspartate ester derivative represented by the formula (1) or (2) may be produced using a raw material other than the optically active aspartic acid, the inexpensive optically active aspartic acid is preferably used as the starting material in view of cost efficiency.

A method for producing the optically active asparagine ester derivative represented by the formula (1) or (2) from the optically active aspartic acid is not particularly limited. One embodiment will be described below.

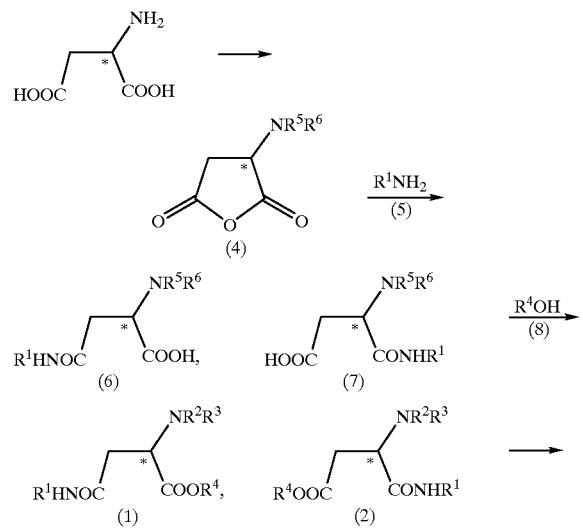

-continued

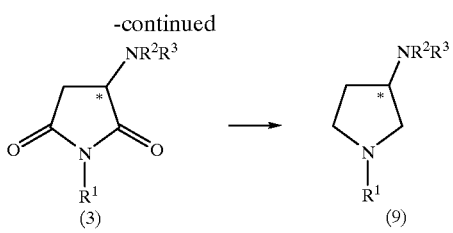

Using the optically active aspartic acid as the starting material, an optically active aspartic anhydride represented by the following formula (4) is produced:

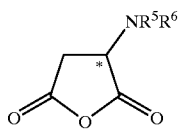

(4)

wherein each of $R^5$ and $R^6$ is a hydrogen atom, an alkyl group, an aryl group, an aralkyl group, an acyl group, an alkoxylcarbonyl group, an alkylsulfonyl group, an arylsulfonyl group, or an aralkylsulfonyl group, $R^5$ and $R^6$ being the same or different. The optically active aspartic acid preferably has an optical purity of 99% e.e. or more.

The optically active aspartic anhydride can be produced by reacting the optically active aspartic acid with an organic acid anhydride. As the organic acid anhydride, a monoacid anhydride, such as formic anhydride, acetic anhydride, or propionic anhydride, or a heteroacid anhydride, such as formic acetic anhydride may be used. Preferably, acetic anhydride or formic acetic anhydride is used, and more preferably, formic acetic anhydride is used.

Preferred examples of the optically active aspartic anhydrides represented by the formula (4) include dialkyl derivatives, such as N-dimethylaspartic anhydride and N-methylbenzylaspartic anhydride; N-acyl derivatives, such as N-formylaspartic anhydride, N-acetylaspartic anhydride, and N-propionylaspartic anhydride; and sulfonyl derivatives, such as N-benzenesulfonylaspartic anhydride. Among these are preferably N-acyl aspartic anhydrides, such as N-formylaspartic anhydride, N-acetylaspartic anhydride, and N-propionylaspartic anhydride because the N-acylaspartic anhydride can be produced in only one step from the optically active aspartic acid and the organic acid anhydride by the reaction described above. Furthermore, since the N-acyl group can be easily deprotected as described below, the N-acylaspartic anhydride is more preferably used when the 3-aminopyrrolidine-2,5-dione derivative in which the amino group in the third position is unsubstituted is produced. More preferably, N-formylaspartic anhydride or N-acetylaspartic anhydride is used, and most preferably, N-formylaspartic anhydride is used.

A known method may be used for the reaction. For example, formic acetic anhydride, which has been preliminarily formed by mixing acetic anhydride and formic acid, and L-aspartic acid are reacted with each other while stirring at 50 to 70° C. for 2 to 5 hours, followed by cooling to room temperature, and toluene is added thereto to crystallize N-formyl-L-aspartic anhydride, and then filtration is performed. In such a step, the reaction smoothly proceeds even without adding an acid catalyst, and under the normal conditions, racemization does not substantially occur.

Next, the optically active aspartic anhydride represented by the formula (4) is reacted with an amine represented by the following formula (5):

$$R^1\text{---}NH_2 \tag{5}$$

wherein $R^1$ is the same as that in the formula (1), to produce an optically active asparagine derivative represented by the following formula (6) or (7), or an acid salt thereof:

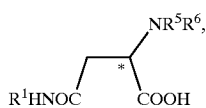

(6)

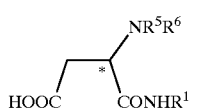

(7)

wherein $R^1$ and the asterisk * are the same as those in the formula (1), and $R^5$ and $R^6$ are the same as those in the formula (4). As the optically active N-aspartic anhydride represented by the formula (4), although either the L-form or the D-form may be used depending on the application, the optical purity is preferably 98% e.e. or more.

As the amine represented by the formula (5), a lower alkylamine having 1 to 4 carbon atoms, such as methylamine or propylamine, an arylamine, such as aniline or anisidine, or an aralkylamine, such as benzylamine, may be used. When the produced optically active asparagine derivative represented by the formula (6) or (7) is continuously used as the raw material for the cyclization and the reduction reaction, the amine may be selected according to the relevant compound. In view of the extraction efficiency by the organic solvent from the reaction system, the deprotection in the subsequent step, etc., benzylamine is preferably used. The amount of the amine used is preferably 0.8 to 5 equivalent, and more preferably 0.99 to 1.5 equivalent relative to the optically active aspartic anhydride represented by the formula (4). If the amount of the amine used is in the above range, both the reaction yield and the cost efficiency are increased. If a large amount of amine is used, the cost efficiency is decreased, and the optically active asparagine derivative represented by the formula (6) or (7) is also easily racemized, which is disadvantageous.

In the reaction, dilution is preferably carried out using an organic solvent. As the solvent, any compound which does not react with the substrate may be used. Examples of the solvent include alcohols, such as ethanol; ethers, such as tetrahydrofuran; aromatic hydrocarbons, such as toluene; alkyl halides, such as chloroform; ketones, such as acetone; carboxylic acids, such as acetic acid; and esters, such as butyl acetate. The preferred solvent is tetrahydrofuran or acetic acid. These solvents may be used alone or as a mixture thereof. Although the amount of the solvent used is not particularly limited as long as the content allows the stirring operation, in view of cost efficiency, the content is usually set so that the substrate content is approximately 5 to 30% by weight. The reaction temperature is preferably 0 to 60° C., and more preferably 10 to 40° C. Since the racemization may also occur if the reaction temperature is increased, the reaction is preferably carried out in the range described above. The reaction time, which depends on the conditions, is usually 1 to 20 hours.

The resultant optically active asparagine derivative represented by the formula (6) or (7) is concentrated or cooled, and then is isolated by filtering the precipitate. The concentrate may be used as it is for the esterification in the subsequent step. By using the method described above, the optically active asparagine derivative represented by the formula (6) or (7) having an optical purity of 90% e.e. or more can be obtained.

Next, the optically active asparagine derivative represented by the formula (6) or (7) is reacted with an alcohol represented by the following formula (8):

$$R^4OH \quad (8)$$

wherein $R^4$ is an alkyl group having 1 to 3 carbon atoms, to produce the optically active aspartate ester derivative represented by the formula (1) or (2). The optically active asparagine derivative represented by the formula (6) may be used alone, the optically active isoasparagine derivative represented by the formula (7) may be used alone, or a mixture of both may be used. The optically active asparagine derivative preferably has an optical purity of 95% e.e. or more.

As the alcohol represented by the formula (8), methanol, ethanol, propanol and isopropanol may be used. Preferably, methanol or ethanol is used, and more preferably, methanol is used. In view of the reaction yield and the reaction time, the amount of the alcohol to be used is preferably 3 to 5 molar times the amount of the optically active asparagine derivative represented by the formula (6) or (7). When the alcohol is also used as a reaction solvent, it is preferably 14 to 30 molar times, and more preferably 15 to 20 molar times. The alcohol may be mixed with an organic solvent. As the organic solvent, an ether such as tetrahydrofuran, an aromatic hydrocarbon such as toluene, a ketone such as acetone, or a halide such as chloroform may be used.

When the esterification is performed, an acid is preferably added thereto. As the concomitant acid, a mineral acid, such as hydrochloric acid or sulfuric acid; a sulfonic acid, such as toluenesulfonic acid; a Lewis acid, such as ferric chloride or zinc chloride, a cation exchange resin, or the like may be used. In such a case, preferably, the reaction is carried out while removing water produced by the esterification from the system. Although the required amount of the acid to be used is the sum of the amount for neutralizing the amino group in the optically active asparagine ester derivative represented by the formula (1) or (2) to be produced and the amount for catalyzing the esterification, in view of the reaction rate, the cost efficiency, and the load in the purification process, the amount of the acid is preferably 1.02 to 1.10 molar times the amount of the optically active asparagine ester derivative.

Instead of the acid, thionyl chloride may be used. In such a case, since water is not produced in the esterification, the reaction process is simplified and the reaction yield is also improved, thus being particularly advantageous. The amount of thionyl chloride to be used is preferably 0.9 to 2.5 molar times, more preferably 1.1 to 2.0 molar times, the amount of the optically active asparagine ester derivative. Since hydrochloric acid by-produced in the reaction and excess thionyl chloride can be removed from the system by simple process, such as concentration, it is possible to use a large amount of thionyl chloride in order to increase the reaction rate.

The reaction temperature is preferably 0 to 80° C., and more preferably 10 to 40° C. Within such a range, the reaction yield is increased and the racemization is inhibited. The reaction time, which depends on the conditions, is usually 1 to 20 hours.

The resultant optically active asparagine ester derivative represented by the formula (1) or (2), or an acid salt thereof is isolated by a conventional method. When a large amount of alcohol is used, vacuum concentration is performed to remove the alcohol and the acid with a low boiling point or excess thionyl chloride, and then an organic solvent, such as tetrahydrofuran, is added again, followed by stirring. The precipitated crystal is filtered or vacuum concentration is performed, followed by drying. Thus, the acid salt of the optically active aspartate ester derivative represented by the formula (1) or (2) is isolated. Additionally, the concentrate obtained by vacuum concentration may be used as it is as a raw material for the cyclization.

By the method described above, it is possible to produce the optically active asparagine ester derivative represented by the formula (1) or (2) having an optical purity of 90% e.e. or more, or an acid salt thereof. If the optically active asparagine derivative represented by the formula (6) or (7) which has been used has an optical purity of 98% e.e. or more, it is possible to obtain the optically active asparagine ester derivative represented by the formula (1) or (2) having an optical purity of 95% e.e. or more. Additionally, although the produced acid salt of the optically active asparagine ester derivative represented by the formula (1) or (2) may be neutralized to form a free optically active asparagine ester derivative, preferably it is preserved as the acid salt since the free optically active asparagine ester derivative is chemically unstable.

In the esterification, when $R^5$ is an acyl group and $R^6$ is a hydrogen atom in the optically active asparagine derivative represented by the formula (6) or (7), i.e., in the case of N-acylasparagine ester derivative, the deprotection of the N-acyl group can be carried out simultaneously with the esterification, which is, therefore, particularly advantageous when a 3-aminopyrrolidine-2,5-dione derivative in which the amino group in the third position is unsubstituted is produced.

By using the optically active asparagine ester derivative represented by the formula (1) or (2) thus obtained as the raw material for the reaction in the present invention, it is possible to produce optically active 3-aminopyrrolidine derivatives and optically active 3-aminopyrrolidine-2,5-dione derivatives which are the intermediates thereof from the inexpensive optically active aspartic acid as the raw material, with a decreased number of process steps, in high yields, and with high optical purity.

The present invention will be described more in detail based on the examples below. However, the present invention is not limited thereto. Additionally, the chemical purity of the optically active asparagine ester derivative represented by the formula (1) or (2) was determined by HPLC. After hydrolysis and conversion to a tartaric acid derivative according to the formula below, the optical purity was determined by HPLC.

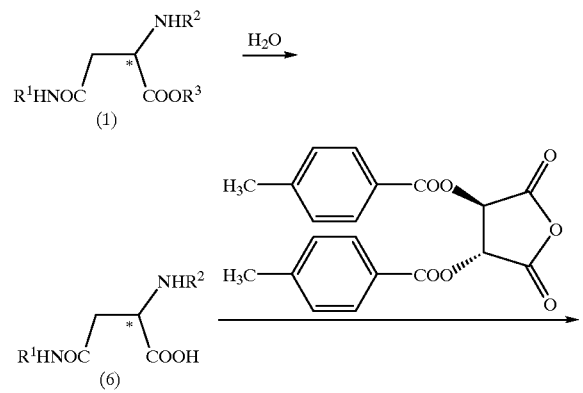

-continued

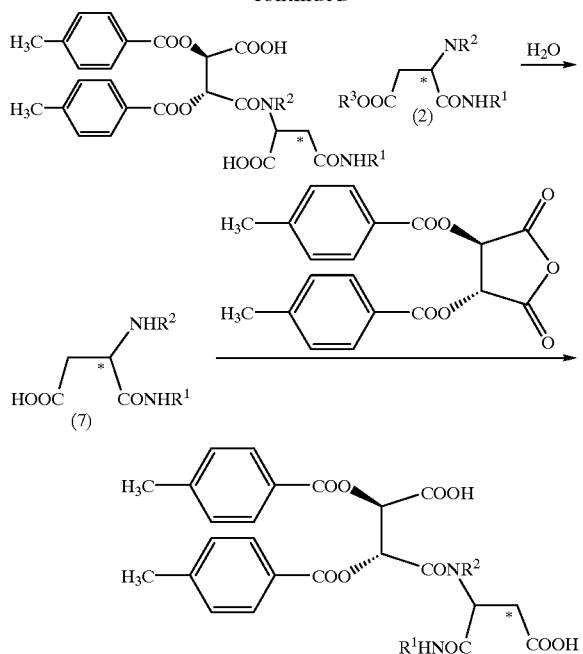

The optical purity was calculated according to the following formula:

$$\text{Optical Purity } (\% \ ee) = \frac{X - Y}{X + Y} \times 100$$

X: L-derivative (or D-derivative)
Y: D-derivative (or L-derivative)
The optical purity of the 1-substituted-3-aminopyrrolidine-2,5-dione derivative represented by the formula (3) was determined by HPLC analysis after the chemical derivation according to the following formula:

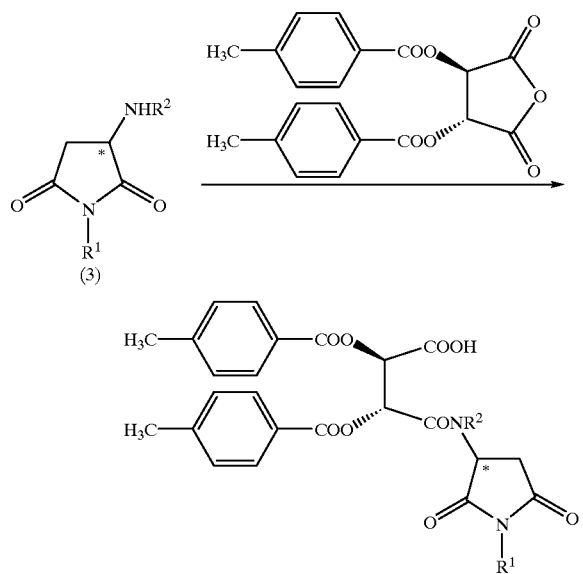

Additionally, the optical purity of the 1-substituted-3-aminopyrrolidine derivative was determined in a manner similar to the above. The reagents used in the examples were commercially available extra-pure reagents.

EXAMPLE 1

Into a 50 ml three-necked flask with a stirrer, a Dimroth condenser, and a thermometer, 2.7 g (0.01 mol; optical purity of 98% e.e.) of L-asparagine benzylamide methyl ester hydrochloride, 8 g of methanol, and 1.0 g of sodium hydrogencarbonate were introduced, followed by stirring at 55° C. for 2 hours. The reaction mixture had a pH of 6.9. By the analysis of the reaction mixture by HPLC, it was confirmed that 1-benzyl-3-aminopyrrolidine-2,5-dione was obtained in the yield of 65% with an optical purity of 81% e.e. 28% of the raw material L-asparagine benzylamidomethyl ester remained.

EXAMPLE 2

The reaction was carried out in a manner similar to that in Example 1 apart from the fact that the solvent for the reaction was changed from methanol to water. By the analysis of the reaction mixture by HPLC, it was confirmed that 1-benzyl-3-aminopyrrolidine-2,5-dione was obtained in the yield of 81% with an optical purity of 85% e.e.

EXAMPLE 3

The reaction was carried out in a manner similar to that in Example 1 apart from the fact that the solvent for the reaction was changed from methanol to 50% methanol aqueous solution. By the analysis of the reaction liquid by HPLC, it was confirmed that 1-benzyl-3-aminopyrrolidine-2,5-dione was obtained in the yield of 88% with an optical purity of 92% e.e.

EXAMPLE 4

Into a 50 ml three-necked flask with a stirrer, a Dimroth condenser, and a thermometer, 5.4 g (0.02 mol; optical purity of 98% e.e.) of L-asparagine benzylamide methyl ester hydrochloride, 8 g of methanol, 8 g of water, and 1.6 g of sodium acetate were introduced, followed by stirring at 55° C. for 0.5 hour. The reaction mixture had a pH of 7.0. By the analysis of the reaction liquid by HPLC, it was confirmed that 1-benzyl-3-aminopyrrolidine-2,5-dione was obtained in the yield of 79% with an optical purity of 83% e.e.

EXAMPLE 5

The reaction was carried out in a manner similar to that in Example 4 apart from the fact that sodium carbonate was used instead of sodium acetate. 1-benzyl-3-aminopyrrolidine-2,5-dione was obtained in the yield of 80% with an optical purity of 85% e.e. The reaction liquid had a pH of 7.0.

EXAMPLE 6

Into a 500 ml four-necked flask with a stirrer, a dropping funnel, a Dimroth condenser, and a thermometer, 112.5 g (1.10 mol) of acetic anhydride were introduced, and 30 g (0.65 mol) of formic acid were added dropwise thereto while stirring at room temperature. After stirring was performed at room temperature for 2 hours, 66.5 g (0.5 mol) of L-aspartic acid with an optical purity of 99.5% e.e. were added thereto, the temperature was increased to 60 to 70° C., and stirring was performed for 10 hours. The temperature was decreased to room temperature while stirring, and 80 g of toluene were further added thereto, followed by stirring. The precipitated crystal was subjected to filtration under reduced pressure and was rinsed with 10 g of toluene. The crystal was subjected to vacuum drying, and thus 60.1 g of N-formyl-L-aspartic anhydride was obtained. The chemical purity was 99%, and the optical purity was 99% e.e. or more.

Into a 200 ml four-necked flask with a stirrer, a dropping funnel, a Dimroth condenser, and a thermometer, 7.2 g (0.05 mol) of the N-formyl-L-aspartic anhydride and 60 g of toluene were introduced, followed by stirring at 20 to 30° C. While maintaining the liquid temperature, 5.4 g (0.05 mol) of benzylamine were added dropwise, and then stirring was performed for 4 hours. The precipitated crystal was subjected to filtration under reduced pressure and was rinsed with 10 g of toluene. The crystal was subjected to vacuum drying, and thus 14.2 g of a mixture of N-formyl-L-asparagine benzylamide (hereinafter referred to as "FAB") and N-formyl-L-isoasparagine benzylamide (hereinafter referred to as "IFAB") were obtained.

Into a 100 ml four-necked flask with a stirrer, a dropping funnel, a Dimroth condenser, and a thermometer, 14.2 g (0.048 mol) of the mixture of FAB and IFAB and 17.3 g (5.4 mol) of methanol were introduced, followed by stirring at 30 to 35° C. While maintaining the liquid temperature at 30 to 35° C., 7.4 g (0.062 mol) of thionyl chloride were added dropwise, and then the temperature was increased to 40 to 45° C., followed by stirring for 3 hours. Vacuum concentration was performed at 40° C., and thus 20.9 g of a mixture of L-asparagine benzylamide methyl ester hydrochloride (hereinafter referred to as "ABN hydrochloride") and L-isoasparagine benzylamide methyl ester hydrochloride (hereinafter referred to as "IABN hydrochloride") were obtained.

Into a 200 ml four-necked flask with a stirrer, a dropping funnel, a Dimroth condenser, and a thermometer, 20.9 g of the mixture of ABN hydrochloride and IABN hydrochloride and 50 g of water were introduced, and 4.0 g of sodium hydrogencarbonate were added thereto while stirring at room temperature. The reaction liquid had a pH of 7.0. The temperature was increased to 55° C. and stirring was performed for 0.5 hour, and then concentrated hydrochloric acid was added thereto to adjust the pH to be 2 or less, followed by cooling to room temperature. At room temperature, 10% sodium hydroxide aqueous solution was added thereto to adjust the pH to be 10 to 11, and then extraction was performed three times using 100 ml of chloroform. All the chloroform layers were subjected to vacuum concentration, and thus 9.5 g of (S)-1-benzyl-3-aminopyrrolidine-2,5-dione were obtained. The optical purity was 91% e.e. The through yield from L-aspartic acid was 78%.

Into a 200 ml four-necked flask with a stirrer, a dropping funnel, a Dimroth condenser, and a thermometer, 9.5 g (46.5mmol) of the (S)-1-benzyl-3-aminopyrrolidine- 2,5-dione, 50 ml of tetrahydrofuran, and 8.8 g (0.23 mol) of sodium borohydride were introduced, and a solution in which 11.5g (0.12 mol) of 98% sulfuric acid were diluted with 20 ml of tetrahydrofuran was added dropwise over approximately 30 minutes while stirring under an ice-bath, and then stirring was performed for 2 hours. The reaction mixture was heated to 65° C. and was stirred for 2 hours. After the reaction was complete, vacuum concentration was performed. 70 g of water was added for dissolution, and 25 g of concentrated hydrochloric acid were added thereto, followed by stirring at 65° C. for 4 hours. The reaction mixture was cooled to room temperature and was neutralized by adding 32 g of 46% sodium hydroxide while stirring. Extraction was performed three times using 100 ml of toluene, and all the toluene layers were simultaneously subjected to vacuum concentration. The concentrate was subjected to vacuum distillation, and thus 7.3 g of (S)-1-benzyl-3-aminopyrrolidine were obtained as the distillate collected at 130 to 133° C./1.3 kPa. As a result of analysis, the chemical purity was 99% and the optical purity was 91% e.e. 7.0 g of the (S)-1-benzyl-3-aminopyrrolidine, 25 ml of methanol, and 0.7 g of 5% Pd/C were introduced into a 100 ml autoclave, and hydrogen was adjusted to have a pressure of 1 MPa. The temperature was increased to 70° C. and stirring was performed for 8 hours. After the reaction was complete, the temperature was decreased to room temperature and the pressure was released. The content was filtered and the mother liquor was concentrated and distilled, and thus 3.2 g of (S)-3-aminopyrrolidine were obtained as the distillate collected at 80 to 83° C./40 kPa. As a result of analysis, the chemical purity was 99% and the optical purity was 90% e.e.

EXAMPLE 7

Into a 2,000 ml four-necked flask with a stirrer, a dropping funnel, a Dimroth condenser, and a thermometer, 336.7 g (1.23 mol; optical purity of 98% e.e.) of D-asparagine benzylamide methyl ester hydrochloride, 407 g of methanol, and 378 g of water were introduced, and 129.4 g (1.54 mol) of powdered sodium hydrogencarbonate were added thereto over 10 minutes while stirring at 30° C. The pH was 6.9. The mixed liquid was heated to 55° C. and stirring was performed for 50 minutes, and then 150 g (1.44 mol) of 35% hydrochloric acid was added to adjust the pH to be 2 or less while maintaining the liquid temperature at 30° C. or less. The reaction mixture was subjected to vacuum concentration to remove methanol, and 763.5 g of the concentrate were obtained. As a result of analysis, it was confirmed that 257.6 g of (R)-1-benzyl-3-aminopyrrolidine-2,5-dione hydrochloride was obtained. The yield was 86.7%. The optical purity was 93% e.e.

EXAMPLE 8

Into a 50 ml three-necked flask with a stirrer, a Dimroth condenser, and a thermometer, 19.7 g (0.1 mol; optical purity of 98% e.e.) of L-isoasparagine methylamidomethyl ester hydrochloride, 50 g of methanol, 50 g of water, and 8.4 g of sodium hydrogencarbonate were introduced, followed by stirring at 30° C. for 2 hours. The reaction liquid had a pH of approximately 6. By the analysis of the reaction liquid by HPLC, it was confirmed that 1-methyl-3-aminopyrrolidine-2,5-dione was obtained in the yield of 75% with an optical purity of 84% e.e. 18% of the raw material L-isoasparagine methylamidomethyl ester remained.

Using a method of the present invention an optically active 3-aminopyrrolidine derivatives which are useful as raw materials for drugs and a optically active 3-aminopyrrolidine-2,5-dione derivatives which are important intermediates thereof can be produced with a decreased number of process steps, in high yields, and with high optical purity.

What is claimed is:

1. A method for making an optically active compound represented by the following formula (3) comprising cyclizing an optically active compound represented by the following formula (1) or (2), or an acid salt thereof:

(1)

R¹HNOC—*—COOR⁴ with NR²R³

(2)

R⁴OOC—*—CONHR¹ with NR²R³

(3)

pyrrolidine-2,5-dione with NR²R³ at 3-position and R¹ on N wherein R¹ is a lower alkyl group having 1 to 4 carbon atoms, an aryl group, or an aralkyl group; each of R² and R³ is a hydrogen atom, an alkyl group, an aryl group, an aralkyl group, an acyl group, an alkoxylcarbonyl group, an alkylsulfonyl group, an arylsulfonyl group, or an aralkylsulfonyl group, R² and R³ being the same or different; R⁴ is an alkyl group having 1 to 3 carbon atoms; and the carbon atom with the asterisk * is an asymmetric center by dissolving said compound represented by formula (1) or (2) or an acid salt thereof in a solvent.

2. A method for making an optically active compound according to claim 1, wherein an alkali metal salt is added in the cyclization.

3. A method for making an optically active compound according to claim 2, wherein the alkali metal salt is an alkali metal acetate, an alkali metal formate, an alkali metal hydrogencarbonate, or an alkali metal carbonate.

4. A method for making an optically active compound according to claim 1, wherein said solvent comprises an aqueous solution having a pH of 3 to 8.

5. A method for making an optically active compound according to claim 1, wherein the cyclization is carried out at 0 to 80° C.

6. A method for making an optically active compound according to claim 1, wherein the optically active compound represented by the formula (1) or (2), or the salt thereof is produced by a process comprising:

reacting L-aspartic acid or D-aspartic acid with an organic acid anhydride to produce an optically active aspartic anhydride represented by the following formula (4):

(4)

aspartic anhydride with NR⁵R⁶ wherein each of R⁵ and R⁶ is a hydrogen atom, an alkyl group, an aryl group, an aralkyl group, an acyl group, an alkoxylcarbonyl group, an alkylsulfonyl group, an arylsulfonyl group, or an aralkylsulfonyl group, R⁵ and R⁶ being the same or different;

reacting the optically active aspartic anhydride represented by the formula (4) with an amine represented by the following formula (5):

$$R^1-NH_2 \quad (5)$$

wherein R¹ is the same as that in the formula (1), to produce an optically active compound represented by the following formula (6) or (7), or an acid salt thereof:

(6)

R¹HNOC—*—COOH with NR²R³

(7)

HOOC—*—CONHR¹ with NR²R³ wherein R¹ and the asterisk * are the same as those in the formula (1), and R⁵ and R⁶ are the same as those in the formula (4); and reacting the optically active compound represented by the formula (6) or (7) with an alcohol represented by the following formula (8):

$$R^4OH \quad (8)$$

wherein R⁴ is an alkyl group having 1 to 3 carbon atoms.

7. A method for making an optically active compound according to claim 6, wherein in the formulae (4), (6), and (7), R⁵ is an acyl group, and R⁶ is a hydrogen atom.

8. A method for making an optically active compound according to claim 6, wherein in the formulae (4), (6), and (7), R⁵ is a formyl group or an acetyl group, and R⁶ is a hydrogen atom, and in the formula (8), R⁴ is a methyl group or an ethyl group.

9. A method for making an optically active compound represented by the following formula (9) comprising reducing via a reducing agent an optically active compound represented by the formula (3) produced by the method according to any one of claims 1 to 8:

(9)

pyrrolidine with NR²R³ at 3-position and R¹ on N wherein R¹, R², R³, and the asterisk * are the same as those in the formula (1).

10. A method for making an optically active compound according to claim 9, wherein said reducing agent comprises a boron hydride.

11. A method for making an optically active compound wherein R¹ is a substituted or unsubstituted benzyl group, comprising hydrogenolyzing an optically active 3-aminopyrrolidine derivative represented by the formula (9), produced by the method according to claim 9.

12. The method according to claim 1, wherein said cyclization is performed in a reaction time in the range of 0.1 to 30 hours.

13. The method according to claim 9, wherein said reduction is performed at a temperature in the range of −20 to 80° C.

14. The method according to claim 9, wherein said reduction is performed in a reaction time of 3 to 20 hours.

15. The method according to claim 10, wherein said boron hydride is one selected from the group consisting of diborane, borane diethyl ether, borane dimethyl sulfide, and sodium borohydride.

16. The method according to claim 11, wherein said hydrogenolysis is performed in the presence of a noble metal catalyst.

17. The method according to claim 16, wherein said noble metal catalyst comprises palladium supported by activated carbon.

18. The method according to claim 11, wherein hydrogen pressure is in the range of 0.1 to 5 MPa.

19. The method according to claim 11, wherein said hydrogenolysis is performed at a reaction temperature in the range of 20 to 100° C.

20. The method according to claim 9, wherein said reduction is performed in an ether solvent.

21. The method according to claim 1, wherein said solvent comprises an aqueous solution comprising a mixture of an organic solvent and water.

22. The method according to claim 20, wherein said ether solvent is selected from the group consisting of tetrahydrofuran, glyme, diglyme, and butanol.

* * * * *